(12) United States Patent
Miller

(10) Patent No.: US 8,083,721 B2
(45) Date of Patent: Dec. 27, 2011

(54) POWER INJECTION VALVE

(75) Inventor: Stephen C. Miller, Queensbury, NY (US)

(73) Assignee: Navilyst Medical, Inc., Marlborough, MA (US)

( * ) Notice: Subject to any disclaimer, the term of this patent is extended or adjusted under 35 U.S.C. 154(b) by 68 days.

(21) Appl. No.: 12/362,004

(22) Filed: Jan. 29, 2009

(65) Prior Publication Data
US 2010/0191185 A1   Jul. 29, 2010

(51) Int. Cl.
*A61M 5/178* (2006.01)
*A61M 5/00* (2006.01)
*A61M 3/00* (2006.01)

(52) U.S. Cl. ............... 604/167.03; 604/43; 604/167.05; 604/186; 604/248; 604/118

(58) Field of Classification Search ............ 604/118, 604/86, 537, 248–256, 186, 207, 43–45
See application file for complete search history.

(56) References Cited

U.S. PATENT DOCUMENTS

| | | |
|---|---|---|
| 2,720,881 A | 10/1955 | Weaver et al. |
| 3,113,586 A | 12/1963 | Edmark, Jr. |
| 3,159,175 A | 12/1964 | MacMillan |
| 3,159,176 A | 12/1964 | Russell et al. |
| 3,477,438 A | 11/1969 | Allen et al. |
| 3,514,438 A | 5/1970 | Nelsen et al. |
| 3,525,357 A | 8/1970 | Koreski |
| 3,621,557 A | 11/1971 | Cushman et al. |
| 3,669,323 A | 6/1972 | Harker et al. |
| 3,673,612 A | 7/1972 | Merrill et al. |
| 3,674,183 A | 7/1972 | Venable et al. |
| 3,811,466 A | 5/1974 | Ohringer |
| 3,955,594 A | 5/1976 | Snow |
| 4,000,740 A * | 1/1977 | Mittleman ............ 604/86 |
| 4,072,146 A | 2/1978 | Howes |

(Continued)

FOREIGN PATENT DOCUMENTS
DE    20208420    10/2002
(Continued)

OTHER PUBLICATIONS

PCT International Search Report—International application No. PCT/US2010/021740, dated Mar. 18, 2010, 2-Pgs.

(Continued)

*Primary Examiner* — Nicholas Lucchesi
*Assistant Examiner* — Rebecca E Eisenberg
(74) *Attorney, Agent, or Firm* — Bingham McCutchen LLP

(57) ABSTRACT

A device for transferring fluids between an internal structure in a living body and an exterior thereof, comprises a housing including a pressure activated lumen extending to a distal end opening to a power injection lumen that extends to a distal port configured for connection to a fluid conduit extending to a target structure within the body and a pressure activated valve extending across the pressure activated lumen and controlling fluid flow therethrough, the pressure activated valve opening to permit fluid flow therethrough into the power injection lumen when a fluid pressure differential thereacross is at least a first predetermined threshold level and remaining sealed when the fluid pressure differential thereacross is less than the first threshold level in combination with a proximal port coupled to the housing for movement between a first position in which a proximal end of the power injection lumen opens to the proximal port and a second position in which a proximal end of the pressure activated lumen opens to the proximal port.

9 Claims, 4 Drawing Sheets

U.S. PATENT DOCUMENTS

| | | | |
|---|---|---|---|
| 4,142,525 A | 3/1979 | Binard et al. | |
| 4,143,853 A | 3/1979 | Abramson | |
| 4,405,316 A | 9/1983 | Mittleman | |
| 4,434,810 A | 3/1984 | Atkinson | |
| 4,447,237 A | 5/1984 | Frisch et al. | |
| 4,468,224 A | 8/1984 | Enzmann et al. | |
| 4,543,087 A | 9/1985 | Sommercorn et al. | |
| 4,552,553 A | 11/1985 | Schulte et al. | |
| 4,610,276 A * | 9/1986 | Paradis et al. | 137/856 |
| 4,610,665 A | 9/1986 | Matsumoto et al. | |
| 4,616,768 A | 10/1986 | Flier | |
| 4,673,393 A | 6/1987 | Suzuki et al. | |
| 4,681,572 A | 7/1987 | Tokarz et al. | |
| 4,692,146 A | 9/1987 | Hilger | |
| 4,790,832 A | 12/1988 | Lopez | |
| 4,798,594 A | 1/1989 | Hillstead | |
| 4,801,297 A | 1/1989 | Mueller | |
| 4,944,726 A | 7/1990 | Hilal et al. | |
| 4,946,448 A | 8/1990 | Richmond | |
| 5,000,745 A | 3/1991 | Guest et al. | |
| 5,009,391 A | 4/1991 | Steigerwald | |
| 5,030,210 A | 7/1991 | Alchas et al. | |
| 5,084,015 A | 1/1992 | Moriuchi | |
| 5,098,405 A | 3/1992 | Peterson et al. | |
| 5,125,893 A | 6/1992 | Dryden | |
| 5,147,332 A | 9/1992 | Moorehead | |
| 5,149,327 A | 9/1992 | Oshiyama | |
| 5,167,638 A | 12/1992 | Felix et al. | |
| 5,169,393 A | 12/1992 | Moorehead et al. | |
| 5,176,652 A | 1/1993 | Littrell | |
| 5,201,722 A | 4/1993 | Moorehead et al. | |
| 5,205,834 A | 4/1993 | Moorehead et al. | |
| 5,249,598 A | 10/1993 | Schmidt | |
| 5,254,086 A | 10/1993 | Moorehead et al. | |
| 5,330,424 A | 7/1994 | Palmer et al. | |
| 5,336,203 A | 8/1994 | Goldhardt et al. | |
| 5,360,407 A | 11/1994 | Leonard et al. | |
| 5,370,624 A | 12/1994 | Edwards et al. | |
| 5,396,925 A | 3/1995 | Poli et al. | |
| 5,399,168 A | 3/1995 | Wadsworth et al. | |
| 5,401,255 A | 3/1995 | Sutherland et al. | |
| D357,735 S | 4/1995 | McPhee | |
| 5,405,340 A | 4/1995 | Fageol et al. | |
| 5,411,491 A | 5/1995 | Goldhardt et al. | |
| 5,453,097 A | 9/1995 | Paradis | |
| 5,454,784 A | 10/1995 | Atkinson et al. | |
| 5,469,805 A | 11/1995 | Gibbs et al. | |
| 5,470,305 A | 11/1995 | Arnett et al. | |
| 5,484,420 A | 1/1996 | Russo | |
| 5,542,923 A | 8/1996 | Ensminger et al. | |
| 5,554,136 A | 9/1996 | Luther | |
| 5,562,618 A | 10/1996 | Cai et al. | |
| 5,571,093 A | 11/1996 | Cruz et al. | |
| 5,575,769 A | 11/1996 | Vaillancourt et al. | |
| 5,624,395 A | 4/1997 | Mikhail et al. | |
| 5,637,099 A | 6/1997 | Durdin et al. | |
| 5,667,500 A | 9/1997 | Palmer et al. | |
| 5,707,357 A | 1/1998 | Mikhail et al. | |
| 5,743,873 A | 4/1998 | Cai et al. | |
| 5,743,884 A | 4/1998 | Hasson et al. | |
| 5,743,894 A | 4/1998 | Swisher | |
| 5,752,938 A | 5/1998 | Flatland et al. | |
| 5,803,078 A | 9/1998 | Brauner | |
| 5,807,349 A | 9/1998 | Person et al. | |
| 5,843,044 A | 12/1998 | Moorehead | |
| 5,853,397 A | 12/1998 | Shemesh et al. | |
| 5,865,308 A | 2/1999 | Qin et al. | |
| 5,944,698 A | 8/1999 | Fischer et al. | |
| 5,984,902 A | 11/1999 | Moorehead | |
| 6,033,393 A | 3/2000 | Balbierz et al. | |
| 6,045,734 A | 4/2000 | Luther et al. | |
| 6,050,934 A | 4/2000 | Mikhail et al. | |
| 6,056,717 A | 5/2000 | Finch et al. | |
| 6,062,244 A | 5/2000 | Arkans | |
| 6,092,551 A | 7/2000 | Bennett | |
| 6,120,483 A | 9/2000 | Davey et al. | |
| 6,152,909 A | 11/2000 | Jones et al. | |
| 6,210,366 B1 | 4/2001 | Sanfilippo | |
| 6,227,200 B1 | 5/2001 | Crump et al. | |
| 6,270,489 B1 | 8/2001 | Wise et al. | |
| 6,306,124 B1 | 10/2001 | Jones et al. | |
| 6,364,861 B1 | 4/2002 | Feith et al. | |
| 6,364,867 B2 | 4/2002 | Wise et al. | |
| 6,375,637 B1 | 4/2002 | Campbell et al. | |
| 6,436,077 B1 | 8/2002 | Davey et al. | |
| 6,442,415 B1 | 8/2002 | Bis et al. | |
| 6,446,671 B2 | 9/2002 | Armenia et al. | |
| 6,508,791 B1 | 1/2003 | Guerrero | |
| 6,551,270 B1 | 4/2003 | Bimbo et al. | |
| 6,610,031 B1 | 8/2003 | Chin | |
| 6,726,063 B2 | 4/2004 | Stull et al. | |
| 6,786,884 B1 | 9/2004 | DeCant et al. | |
| 6,874,999 B2 | 4/2005 | Dai et al. | |
| 6,953,450 B2 | 10/2005 | Baldwin et al. | |
| 6,994,314 B2 | 2/2006 | Garnier et al. | |
| 7,081,106 B1 | 7/2006 | Guo et al. | |
| 7,291,133 B1 | 11/2007 | Kindler et al. | |
| 7,316,655 B2 | 1/2008 | Garibotto et al. | |
| 7,435,236 B2 | 10/2008 | Weaver et al. | |
| 7,601,141 B2 | 10/2009 | Dikeman et al. | |
| 7,637,893 B2 | 12/2009 | Christensen et al. | |
| 7,758,541 B2 * | 7/2010 | Wallace et al. | 604/103.01 |
| 2001/0023333 A1 | 9/2001 | Wisse et al. | |
| 2001/0037079 A1 | 11/2001 | Burbank et al. | |
| 2002/0016584 A1 | 2/2002 | Wise et al. | |
| 2002/0121530 A1 | 9/2002 | Socier | |
| 2002/0165492 A1 | 11/2002 | Davey et al. | |
| 2002/0193752 A1 | 12/2002 | Lynn | |
| 2003/0122095 A1 | 7/2003 | Wilson et al. | |
| 2004/0034324 A1 | 2/2004 | Seese et al. | |
| 2004/0064128 A1 | 4/2004 | Raijman et al. | |
| 2004/0186444 A1 | 9/2004 | Daly et al. | |
| 2004/0193119 A1 | 9/2004 | Canaud et al. | |
| 2004/0267185 A1 | 12/2004 | Weaver et al. | |
| 2005/0010176 A1 | 1/2005 | Dikeman et al. | |
| 2005/0027261 A1 | 2/2005 | Weaver et al. | |
| 2005/0043703 A1 | 2/2005 | Nordgren | |
| 2005/0049555 A1 | 3/2005 | Moorehead et al. | |
| 2005/0149116 A1 | 7/2005 | Edwards et al. | |
| 2005/0171490 A1 | 8/2005 | Weaver et al. | |
| 2005/0171510 A1 | 8/2005 | DiCarlo et al. | |
| 2005/0283122 A1 | 12/2005 | Nordgren | |
| 2006/0129092 A1 | 6/2006 | Hanlon et al. | |
| 2006/0135949 A1 | 6/2006 | Rome et al. | |
| 2006/0149211 A1 | 7/2006 | Simpson et al. | |
| 2007/0161970 A1 | 7/2007 | Moorehead et al. | |
| 2007/0276313 A1 | 11/2007 | Moorehead et al. | |
| 2008/0108956 A1 | 5/2008 | Lynn et al. | |
| 2009/0292252 A1 | 11/2009 | Lareau et al. | |

FOREIGN PATENT DOCUMENTS

| | | |
|---|---|---|
| EP | 0128625 | 12/1984 |
| EP | 0930082 | 7/1999 |
| EP | 1016431 | 7/2000 |
| FR | 2508008 | 12/1982 |
| FR | 2718969 | 10/1995 |
| GB | 966137 | 8/1964 |
| GB | 2102398 | 2/1983 |
| WO | WO-89/02764 | 4/1989 |
| WO | WO-92/06732 | 4/1992 |
| WO | WO-95/16480 | 6/1995 |
| WO | WO-96/17190 | 6/1996 |
| WO | WO-96/23158 | 8/1996 |
| WO | WO-96/41649 | 12/1996 |
| WO | WO-97/23255 | 7/1997 |
| WO | WO-97/26931 | 7/1997 |
| WO | WO-98/22178 | 5/1998 |
| WO | WO-99/42166 | 8/1999 |
| WO | WO-00/06230 | 2/2000 |
| WO | WO-00/44419 | 8/2000 |
| WO | WO-01/74434 | 10/2001 |
| WO | WO-03/084832 | 10/2003 |
| WO | WO-2005/023355 | 3/2005 |

OTHER PUBLICATIONS

Asch, "Venous access: options, approaches and issues," Can Assoc. Radiol J., vol. 52, No. 3 pp. 153-164 (2001).

Herts et al., "Power injection of contrast media using central venous catheters: feasibility, safety, and efficacy," AJR Am. J. Roentgenol., vol. 176, No. 2, pp. 447-453 (2001).

Roth et al., "Influence of radiographic contrast media viscosity to flow through coronary angiographic catheters," Cathet. Cardiovasc. Diagn., vol. 22, No. 4, pp. 290-294 (1991).

Carlson et al., "Safety considerations in the power injection of contrast media via central venous catheters during computered tomogrphic examinations," Invest. Radiol., vol. 27, No. 5, p. 337-340 (1992).

Kaste et al., "Safe use of powr injectors with central and peripheral venous access devices for pediatrict CT," Pediatr. Radiol., vol. 26, No. 8, pp. 449-501 (1996).

Herts et al., "Power injection of intravenous contrast material through central venous catheters for CT: in vitro evaluation," Radiology, vol. 200, No. 3, pp. 731-735 (1996).

Rivitz et al., "Power injection of peripherally inserted central catheters," J. Vasc. Interv. Radiol., vol. 8, No. 5, pp. 857-863 (1997).

Rogalla et al., Safe and easy power injection of contrast material through a central line, Eur. Radiol., vol. 8, No. 1, pp. 148-149 (1998).

Williamson et al., "Assessing the adequacy of peripherally inserted central catheters for power injection of intravenous contrast agents for CT," J. Comput. Assist. Tomogr., vol. 25, No. 6, pp. 932-937 (2001).

Chahous et al., "Randomized comparison of coronary angiography using 4F catheters: 4F manual versus 'Acisted' power injection technique," Catheter Cardiovasc. Interv., vol. 53, No. 2, pp. 221-224 (2001).

Walsh et al., "Effect of contrast agent viscosity and injection flow velocity on bolus injection pressures for peripheral venous injection in first-pass myocardial perfusion studies," Technol. Health Care, vol. 10, No. 1, pp. 57-63 (2002).

Saito et al., "Diagnostic brachial coronary arteriography using a power-assisted injector and 4 French catheters with new shamps," J. Invasive Cardiol., vol. 9, No. 7, pp. 461-468 (1997).

* cited by examiner

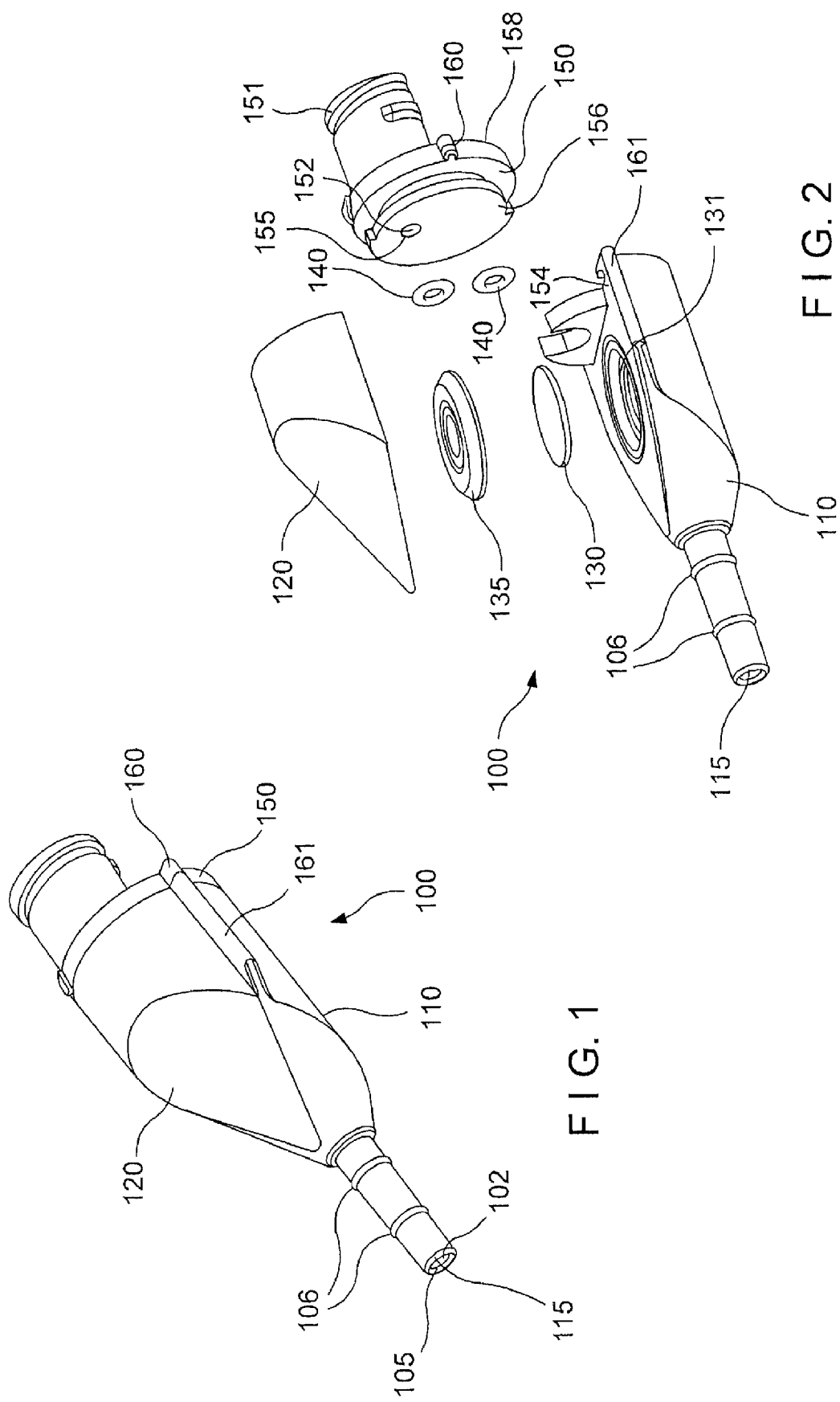

POWER INJECTION VALVE

BACKGROUND

Procedures requiring the use of peripherally inserted central catheters ("PICC") often employ pressure activated valves to seal these catheters when not in use. Such pressure activated valves are designed to remain closed during normal pressure fluctuations between uses to prevent leakage and backflow which may lead to occlusions and/or infections. However, these valves have often been unsuitable for the injection of fluids at high pressures or volumes.

SUMMARY OF THE INVENTION

The present invention is directed to a device for transferring fluids between an internal structure in a living body and an exterior thereof, comprises a housing including a pressure activated lumen extending to a distal end opening to a power injection lumen that extends to a distal port configured for connection to a fluid conduit extending to a target structure within the body and a pressure activated valve extending across the pressure activated lumen and controlling fluid flow therethrough, the pressure activated valve opening to permit fluid flow therethrough into the power injection lumen when a fluid pressure differential thereacross is at least a first predetermined threshold level and remaining sealed when the fluid pressure differential thereacross is less than the first threshold level in combination with a proximal port coupled to the housing for movement between a first position in which a proximal end of the power injection lumen opens to the proximal port and a second position in which a proximal end of the pressure activated lumen opens to the proximal port.

The present invention is further directed to a method for transferring fluids between a target internal structure of a living body and an exterior of the body, the method comprising connecting to a proximal end of a fluid conduit extending into the body to the target structure a distal port of a housing opening to a power injection lumen thereof, the housing including a pressure activated lumen extending to a distal end opening to the power injection lumen with a pressure activated valve opening to permit fluid flow therethrough into the power injection lumen when a fluid pressure differential thereacross is at least a first predetermined threshold level and remaining sealed when the fluid pressure differential thereacross is less than the first threshold level and moving a proximal port of the housing to a first position in which the proximal port is fluidly coupled to the power injection lumen in combination with supplying a first fluid to the proximal port at a power injection pressure greater than the first threshold level, moving the proximal port of the housing to a first position in which the proximal port is fluidly coupled to the pressure activated lumen and supplying a second fluid to the proximal port at a pressure greater than the first threshold level and less than the power injection pressure.

BRIEF DESCRIPTION OF THE DRAWINGS

The accompanying drawing illustrates the design of the present invention wherein:

FIG. 1 shows a first view of an apparatus according to a first embodiment of the present invention;

FIG. 2 shows an exploded view of the device of FIG. 1;

DETAILED DESCRIPTION

Figure 3:
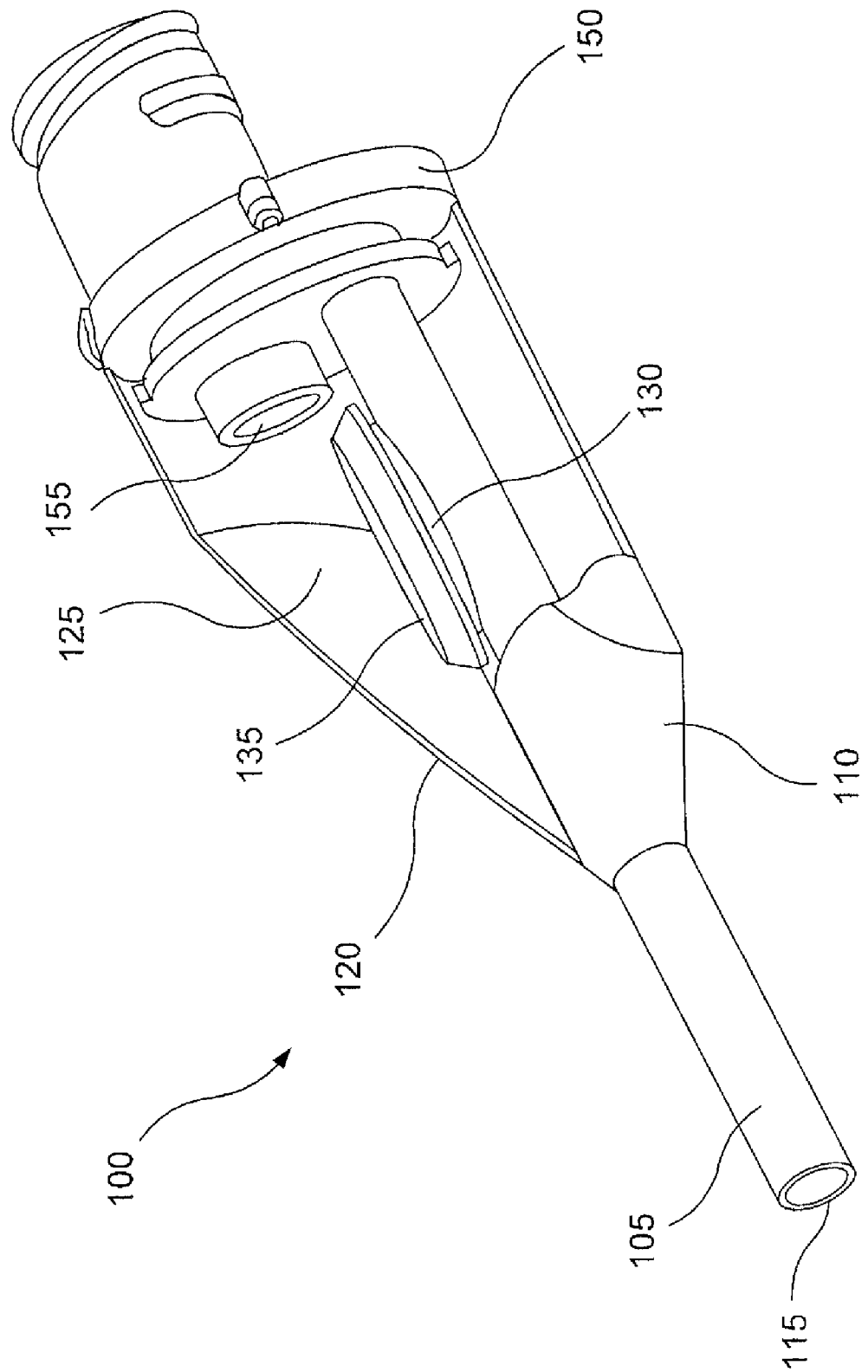
FIG. 3 shows an internal view of the device of FIG. 1.

The present invention, which may be further understood with reference to the following description and the appended drawings, relates to a system and method for high pressure and high volume injection without damaging a pressure activated valve. In particular, the present invention relates to the selective engagement for high pressure and high volume injection of separate lumens within a device employed in conjunction with a catheter (e.g., a PICC catheter) with at least one of the lumens employing a pressure activated valve.

Presently available pressure activated valves are generally unable to sustain the high pressures and flow rates associated with power injection (e.g., of contrast media). An exemplary embodiment of the present invention seeks to alleviate this problem by incorporating with a pressure activated valve a bypass feature allowing power injection without damaging the pressure activated valve.

As shown in FIGS. 1-8, a port 100 according to a first embodiment of the invention includes two passages which may be selectively engaged to select either power injection or standard infusion/withdrawal of fluids. The port 100 comprises a base 110 and a cover 120 joined together, for example, via any known means such as bonding, welding, friction fit, etc. Protruding distally from the port 100 is an elongated tubular body 105 with a lumen 115 extending therethrough and into the base 110, as will be described in greater detail below. It is noted that the term proximal as referred to herein refers to a direction approaching a user or point of user access to the device while distal refers to a direction toward an interior of the body of the patient.

The tubular body 105 is provided with a barbed fitting comprising a series of ridged portions 106 designed to frictionally engage a catheter disposed thereover. Specifically, the ridged portions 106 are formed with a diameter sized to frictionally engage inner walls of a catheter, thereby firmly securing the catheter to the port 100. Accordingly, to mate to the port 100, a catheter is guided over the tubular body 105 to a proximal-most position and frictionally retained thereon. In an alternate embodiment, the tubular body 105 may be insert molded on the catheter, as those skilled in the art will understand.

As shown in the exploded view of FIG. 2, a silicone disk 130 is provided in the port 100, in engagement with a correspondingly sized recess 131 in the base 110 which opens to the lumen 115. The silicone disk 130 effectively regulates the pressure and flow of fluids passing therethrough the port 100. As would be understood by those skilled in the art, the disk 130 may be formed in any desired configuration to obtain desired flow configurations. For example, the disk 130 and a slot or slots therethrough may be formed as shown for any of slitted membranes disclosed in U.S. patent application Ser. No. 10/768,571 entitled "Pressure Activated Safety Valve With Anti-Adherent Coating" filed on Jan. 29, 2004 to Weaver, et al. (the '571 app.); U.S. application Ser. No. 10/768,565 entitled "Pressure Activated Safety Valve With High Flow Slit" filed on even day herewith naming Karla Weaver and Paul DiCarlo as inventors, and U.S. application Ser. No. 10/768,629 entitled "Stacked Membrane For Pressure Actuated Valve" filed on even day herewith naming Karla Weaver and Paul DiCarlo as inventors, and U.S. application Ser. No. 10/768,855 entitled "Pressure Actuated Safety Valve With Spiral Flow Membrane" filed on even day herewith naming Paul DiCarlo and Karla Weaver as inventors, and U.S. application Ser. No. 10/768,479 entitled "Dual Well Port Device" filed on even day herewith naming Katie Daly, Kristian DiMatteo and Eric Houde as inventors. The entire disclosures of each of these applications are hereby incorporated by reference in this application. The silicone disk 130 is held in place over the recess 131 via a disk retainer 135 which engages a periphery thereof. When the cover 120 is mounted to the base 110, a portion of the cover 120 engages the disk retainer 135 applying pressure against the disk 130 to hold the disk 130 against a periphery of the recess 131 and prevent the silicone disk 130 from being moved therefrom.

A rotating luer 150 engages a proximal end of the base 110 at a proximal end of the port 100, as further shown in FIG. 3. The rotating luer 150 includes a lumen 155 extending therethrough from a proximal end 151 to a distal end 152 and at least two tabs 160 extending therefrom about a circumference of an end plate 158 of the luer 150 which preferably forms a substantially continuous surface with the portion of the port 100 (i.e., proximal ends of the base 110 and the cover 120 regardless of a rotational orientation of the luer 150. The tabs 160 indicate an alignment of the lumen 155 in relation to the two lumens 115 and 125 of the port 100, as will be described in greater detail below. The luer 150 also includes a disk-shaped mating projection 156 which is received within a correspondingly shaped and sized slot 154 to rotatably secure the luer 150 to the base 110.

Two O-rings 140 are provided between the rotating luer 150 and the upper and lower body portions 120, 110 to provide a fluid seal therebetween. However, those skilled in the art will understand that any number of O-rings may be provided in the device and these O-rings may vary in thickness and size to obtain the desired seal. The O-rings may exhibit elastomeric properties and may, in an exemplary embodiment, be received in recesses formed on a proximal faces of the base 110 and the cover 120 around proximal openings to the lumens 115, 125, respectively.

As shown in FIG. 3, when in a pressure activated position, the lumen 155 of the luer 150 is aligned with the lumen 125 of the cover 120 which opens to the disk 130. As would be understood by those skilled in the art, when a pressure differential between the lumen 125 and the lumen 115 exceeds a predetermined threshold, edges of the slit(s) in the disk 130 are moved apart from one another and fluid will flow through the disk 130 into the lumen 115 to a catheter attached thereto. When the pressure differential remains below the predetermined threshold, the disk 130 remains sealed preventing fluid flow from the lumen 115 to the lumen 125.

Figure 6:
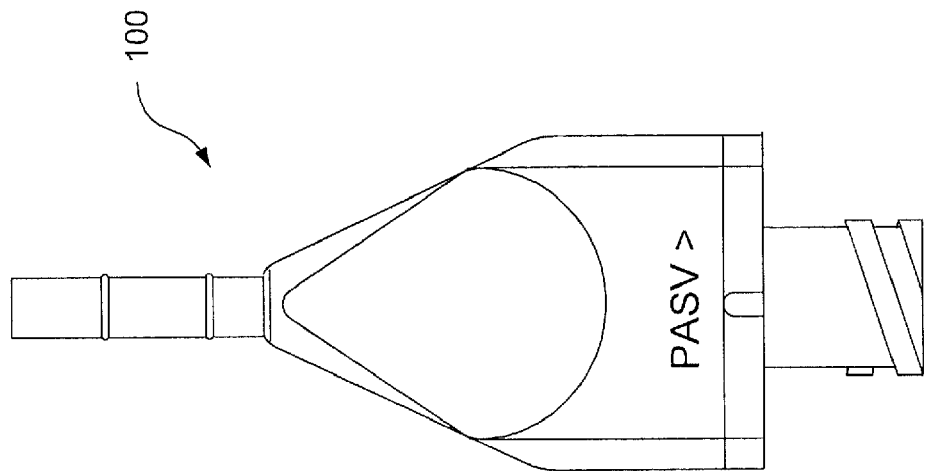
FIG. 6 shows a top view of the device of FIG. 1.
Figure 5:
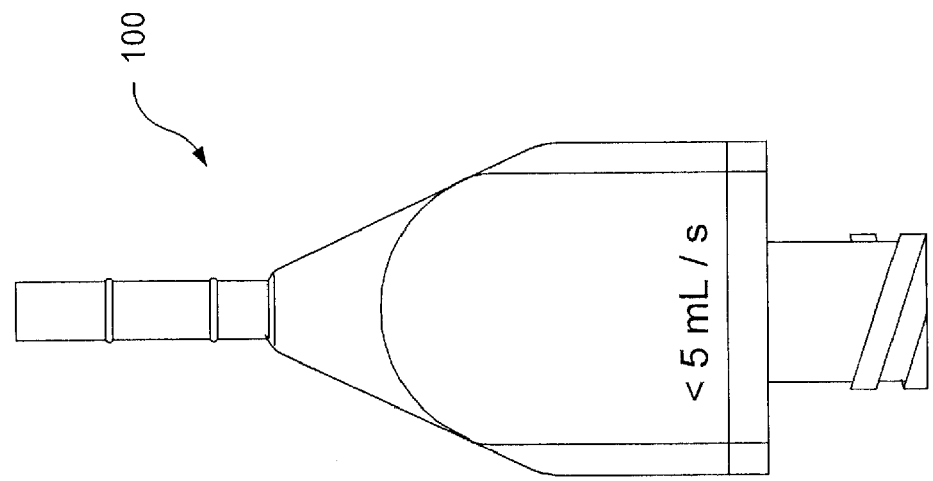
FIG. 5 shows a bottom view of the device of FIG. 1.
Figure 4:
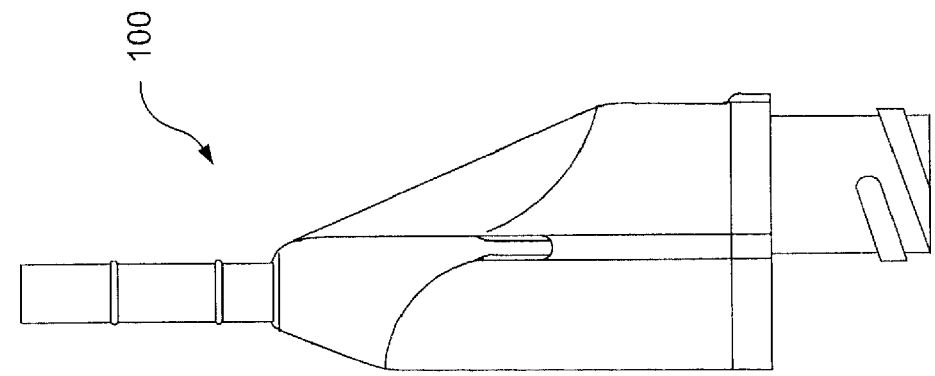
FIG. 4 shows a side view of the device of FIG. 1.
Figure 7:
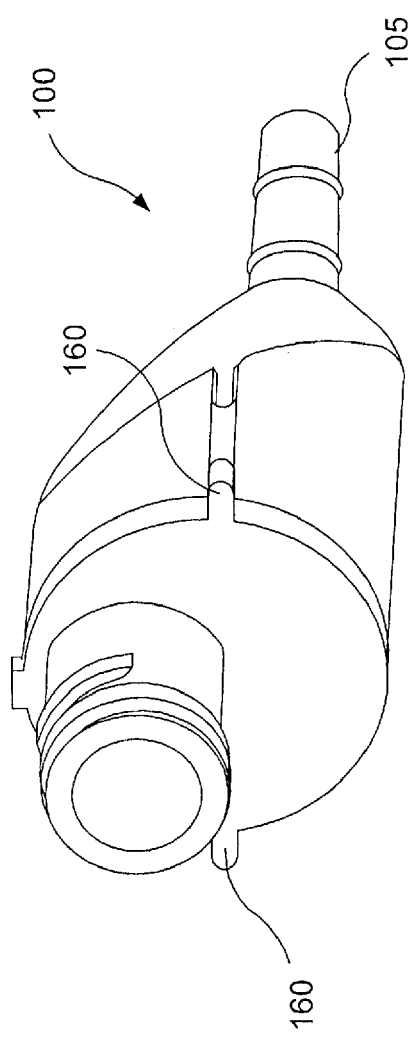
FIG. 7 shows a perspective view of the device of FIG. 1 in a position permitting flow through a pressure activated valve.

In order to configure the port 100 in the pressure activated position as also shown in FIGS. 6 and 7, a user of the port 100 rotates the luer 150 until the tabs 160 are aligned with corresponding projections (e.g., projections 161) on the port distal body of the port 100 (i.e., the base 110 and/or the cover 120) to an indicated pressure activated position. Specifically, the proximal portion of the port 100 may be labeled to indicate the locations of the lumens 115 and 125, as shown in FIGS. 5 and 6. A physician may then rotate the proximal portion of the port 100 to align the tabs 160 with the projections 161. Rotating the proximal portion of the port 100 in either a clockwise or counter-clockwise direction until the lumen 155 aligns with the desired lumen of the port 100 engages the desired one of the lumens 125 and 115. It is further noted that, when the tabs 160 are not aligned with the projections 161, the port 100 is in an off position with both of the lumens 115 and 125 sealed to prevent the flow of fluid into or out of the proximal portion of the device.

Once the pressure activated valve has been selected, the flow of fluid through the port 100 is guided through the pressure activated valve, as detailed above, with fluid entering the port 100 through an externally attached fluid source via an attachment means shown at the proximal end 151 of the rotating luer 150. The fluid flows through the lumen 155 and into the lumen 125 and, when the pressure differential exceeds the predetermined threshold level, past the silicone disk 130 into the lumen 115 via the recess 131. The fluid is passes through the lumen 115 toward the elongated tubular body 105 as flow toward the proximal end of the lumen 115 is prevented by the fluid-tight seal formed by the distal face of the rotating luer 150 which covers the proximal opening to the lumen 115 when the pressure activated valve has been selected. The fluid flows out of the distal opening of the elongated tubular body 105 to a targeted site in the body via a catheter or other device attached to the tubular body portion 105 as would be understood by those skilled in the art.

Figure 8:
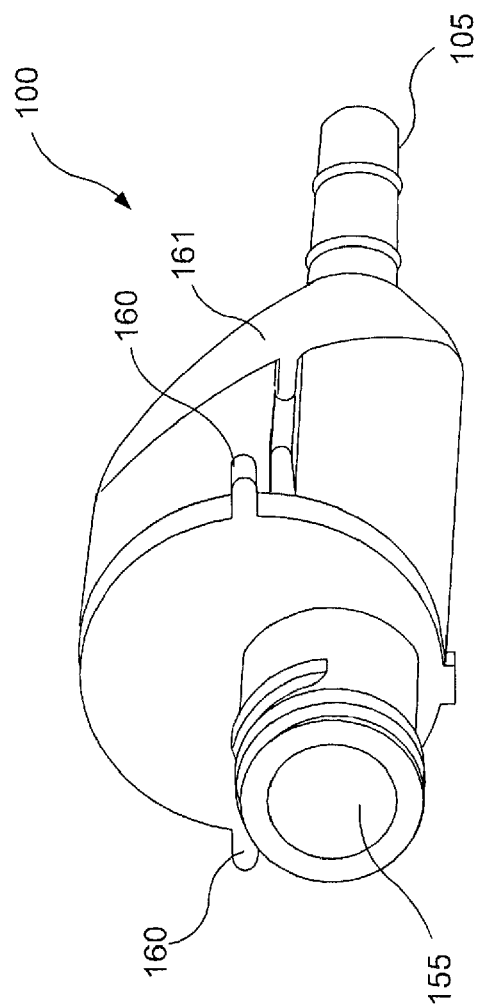
FIG. 8 shows a perspective view of the device of FIG. 1 in a normal flow position.

Alternatively, if the "<5 mL/s" marker is selected, as shown in FIGS. 5 and 8, the lumen 155 is connected directly to the lumen 115 located inside the base 110 of the port 100. An external high pressure or high volume fluid source may then be attached to a proximal end of the port 100 so that high pressure and/or high volume fluid (e.g., at flow rates and pressures suitable for the power injection of contrast media) supplied to the port 100 passes directly through the lumen 115 to the distal opening in the body 105 and into the catheter without passing through the disk 130. It is further noted that the diameter of the lumen 155 may be substantially similar to the diameter of the lumen 115 to allow for an undeterred flow of fluid therethrough.

The present invention has been described with respect to particular designs and embodiments. However, those skilled in the art will understand that the described exemplary embodiments of the present invention may be altered without departing from the spirit or scope of the invention. For example, the port 100 may be altered in geometry, with the diameters of the either of the lumens 115, 125 and 155 increased or decreased to accommodate the requirements of a patient or procedure for which they are intended. Furthermore, a design may be incorporated with each of the lumens 115 and 125 identified by a different color or pattern of colors, eliminating the need for written markings on the outer body of the port 100.

It is to be understood that these embodiments have been described in an exemplary manner and are not intended to limit the scope of the invention which is intended to cover all modifications and variations of this invention that come within the scope of the appended claims and their equivalents. The specifications are, therefore, to be regarded in an illustrative rather than a restrictive sense.

What is claimed is:

1. A device for transferring fluids between an internal structure in a living body and an exterior thereof, comprising:
   a housing including a pressure activated lumen and a power injection lumen, wherein the power injection lumen extends to a distal port configured for connection to a fluid conduit extending to a target structure within the body;
   a pressure activated valve configured to fluidly connect the pressure activated lumen to the power injection lumen and controlling fluid flow therebetween, the pressure activated valve opening to permit fluid flow therethrough into the power injection lumen when a fluid pressure differential thereacross is at least a first predetermined threshold level and remaining sealed when the fluid pressure differential thereacross is less than the first threshold level; and a proximal port coupled to the housing for movement between a first position in which a proximal end of the power injection lumen opens to the proximal port and a second position in which a proximal end of the pressure activated lumen opens to the proximal port.

2. The device according to claim 1, wherein, when in the first position, the proximal port seals the proximal end of the pressure activated lumen and, when in the second position, the proximal port seals the proximal end of the pressure injection lumen.

3. The device according to claim 2, wherein, when in a third position, the proximal port seals the proximal ends of both the pressure activated and power injection lumens.

4. The device according to claim 1, wherein the pressure activated valve includes a slitted flexible membrane.

5. The device according to claim 4, wherein the slitted flexible membrane is formed of silicone.

6. The device according to claim 1, wherein the pressure activated valve opens to permit fluid flow therethrough from the power injection lumen into the pressure activated lumen at a second threshold level higher than the first threshold level.

7. The device according to claim 6, wherein the pressure activated valve is constructed so that the second threshold level is higher than a pressure differential to which the valve will be subjected during power injection via the power injection lumen.

8. The device according to claim 1, wherein the proximal port is rotatably coupled to a proximal portion of the housing for rotation between the first and second positions.

9. The device according to claim 1, wherein the distal port is adapted to couple to a catheter.

* * * * *